(12) United States Patent
Kirsch et al.

(10) Patent No.: US 6,763,832 B1
(45) Date of Patent: Jul. 20, 2004

(54) DEVICE AND METHOD FOR THE ADMINISTRATION OF OXYGEN

(75) Inventors: Wolff M. Kirsch, Redlands, CA (US); Albert W. Farnsworth, Andes, NY (US); Yong Hua Zhu, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 09/561,380

(22) Filed: Apr. 27, 2000

Related U.S. Application Data (60) Provisional application No. 60/131,297, filed on Apr. 27, 1999.

(51) Int. Cl.[7] .......................... A61M 15/08; A62B 7/00
(52) U.S. Cl. .......................... 128/207.18; 128/206.25; 128/203.22; 128/206.11
(58) Field of Search .................... 128/207.18, 206.25, 128/203.22, DIG. 26, 206.11, 200.26, 200.24; 137/601.14

(56) References Cited

U.S. PATENT DOCUMENTS

| | | | |
|---|---|---|---|
| 2,245,969 A | * | 6/1941 | Francisco et al. ....... 128/207.18 |
| 2,693,800 A | | 11/1954 | Caldwell |
| 2,931,358 A | * | 4/1960 | Sheridan ................ 128/207.18 |
| 3,643,660 A | | 2/1972 | Hudson et al. ............. 128/206 |
| 3,726,275 A | * | 4/1973 | Jackson et al. ........ 128/207.18 |
| 3,754,552 A | * | 8/1973 | King ..................... 128/207.18 |
| 3,802,431 A | | 4/1974 | Farr .......................... 128/206 |
| 4,106,505 A | | 8/1978 | Salter et al. ................ 128/206 |
| 4,278,082 A | | 7/1981 | Blackmer |
| 4,422,456 A | * | 12/1983 | Tiep ....................... 128/207.17 |
| 4,584,996 A | * | 4/1986 | Blum .................... 128/204.21 |
| 4,609,011 A | * | 9/1986 | Uehara .................. 137/624.15 |
| 4,660,555 A | | 4/1987 | Payton .................. 128/207.18 |
| 4,782,832 A | | 11/1988 | Trimble et al. |
| 4,790,308 A | * | 12/1988 | Weichselbaum ....... 128/207.18 |
| 4,808,160 A | * | 2/1989 | Timmons et al. ...... 128/207.18 |
| 4,836,200 A | | 6/1989 | Clark .................... 128/207.18 |
| 5,025,805 A | | 6/1991 | Nutter ................... 128/207.18 |
| 5,099,836 A | | 3/1992 | Rowland et al. |
| 5,193,534 A | | 3/1993 | Peppler ................. 128/207.18 |
| 5,315,989 A | | 5/1994 | Tobia |
| 5,335,656 A | * | 8/1994 | Bowe et al. ........... 128/207.18 |
| 5,438,979 A | | 8/1995 | Johnson, Jr. et al. ... 128/207.18 |
| 5,509,409 A | | 4/1996 | Weatherholt ........... 128/207.28 |
| 5,513,635 A | * | 5/1996 | Bedi ...................... 128/207.18 |
| 5,533,506 A | * | 7/1996 | Wood .................... 128/200.26 |
| 5,535,739 A | * | 7/1996 | Rapoport et al. ...... 128/204.23 |
| 5,575,282 A | | 11/1996 | Knoch et al. .......... 128/204.18 |
| 5,645,058 A | | 7/1997 | Odom ................... 128/207.18 |
| 5,697,364 A | * | 12/1997 | Chua et al. ............ 128/204.21 |
| 5,752,511 A | * | 5/1998 | Simmons et al. ...... 128/206.11 |
| 5,931,854 A | * | 8/1999 | Dillon ................... 606/204.45 |
| 6,093,169 A | * | 7/2000 | Cardoso .................. 604/94.01 |

FOREIGN PATENT DOCUMENTS

WO     WO 92/20392     11/1992

\* cited by examiner

*Primary Examiner*—Weilun Lo
*Assistant Examiner*—Darwin P. Erezo
(74) *Attorney, Agent, or Firm*—Knobbe, Martens, Olson & Bear, LLP.

(57) ABSTRACT

A nasal cannula is provided having a first and second nasal plug connected to a gas supply such as oxygen. A holder frictionally engages each nasal plug and a connector connects the two holders. The plugs are movable along the length of the connector to allow adjustment of the spacing between nasal plugs to accommodate a person's nostrils but with sufficient friction to retain the selected position. The plugs are rotatable around the longitudinal axis of the connector to adjust the orientation of the plug within a nostril relative to a patient's face, but with sufficient friction to retain the selected position. One of the connector or holder is removably fastened to the patient's face. A regulator is interposed in the gas supply to vary the flow rate and pressure to meet predetermined patterns.

35 Claims, 4 Drawing Sheets

DEVICE AND METHOD FOR THE ADMINISTRATION OF OXYGEN

CROSS-REFERENCE TO RELATED APPLICATION

This application claims priority under 35 U.S.C. 119(e) to U.S. Provisional Application Serial No. 60/131,297 filed on Apr. 27, 1999.

FIELD OF THE INVENTION

The present invention relates to a nasal cannula device and method for use in the administration of oxygen into the nasal passages of a person requiring reparatory supplementation.

BACKGROUND OF THE INVENTION

The use of nasal cannulas has been one of the most efficient methods of administering therapeutic oxygen or other gases to patients. When a patient is required to have prolonged oxygen administration, it is necessary that the cannula be worn both during awakening hours as well as sleeping hours. But continued contact between the body and cannula can cause discomfort and irritation.

An existing nasal cannula has a fixed spacing between two nasal extensions or nasal plugs. Because the spacing is fixed, the patient can not shift the contact position to reduce the discomfort. Moreover, the sharp edges of the nasal extension tips can rub against the sensitive skin inside the nostrils and cause more irritation. Another problem comes from the constant oxygen flow which creates a sore spot on the surface of the nasal passageways.

There is thus a need for an improved nasal cannula system to solve the above mentioned problems and meet the needs of the patients. In particular, there is thus a need to adjust the position of the nasal plugs inside the nostrils along the nasal channel to reduce discomfort.

SUMMARY OF THE INVENTION

This invention is directed to an improved apparatus and method for oxygen administration. The improvement discussed here can also be applied to other gas administration. An improved nasal cannula comprises a pair of separate nasal plugs. A nasal plug connector connects the two plugs and also functions as a holder for attaching the cannula to the patient's face. A pair of auxiliary oxygen supply tubes are connected to one of the inlet ends of the nasal cannula. A main oxygen supply line connects both inlet ends of the two auxiliary tubes and the oxygen source, for example, an oxygen tank, an oxygen vaporizer, and the like.

Each of the two nasal plugs is a generally L-shaped tube where the shorter leg of the tube goes into the patient's nostril for delivery of oxygen or other gases. The longer leg has a distal end adapted to be placed in fluid communication with the oxygen supply, such as one of the auxiliary oxygen tubes. The nasal plugs, as well as the auxiliary oxygen tubes, are advantageously made of standard medical tubing material which is suitable for injection molding. A soft and flexible material such as polyvinylchloride is useful.

The two nasal plugs are movably mounted relative to each other by a connector which has two holders connected by a bridge or bar portion. Each holder advantageously comprises a holding portion connected to an attaching portion. Advantageously, the overall holder resembles a flexible member generally shaped like the number "6". Each of the holders has a long and generally straight back or attaching portion connected to a curved annular or holding portion that is curved back toward the interior side of the back portion. The annular part of the 6-shaped member may form a closed loop by connecting the end of the curve to the back portion. A slot can also be advantageously formed in the annular portion at a position close to the back portion. The slot in the annular portion provides an easy access for inserting and removing the nasal plugs. The annular portion is preferably made of a material which is flexible enough to allow the long leg of each L-shaped nasal plug to be inserted or removed, and is strong enough to hold the cannula during use.

The connector is preferably positioned in the patient's philtrum area with the bar portion generally parallel with the patient's upper lip. The attaching portion of each 6-shaped member is in contact with the patient's face with the holding portion extending away from the face. The long leg of each nasal plug passes through one of the loops from center to the side while the short legs point upward into the patient's nostrils. The holding portion of each 6-shaped member has an elastomeric surface around at least a portion of the loop to frictionally engage one of the nasal plugs. This frictional connection allows the two nasal plugs to be adjusted relative to each other to change the spacing between them. It also allows rotation along the longitudinal axis of the long legs to achieve a proper orientation to center the plugs within the nostrils. The bar portion bridging the two 6-shaped members functions as a support for the nasal cannula to maintain their relative position on the face.

Once the preferred depth of the plugs inside the nostrils is achieved, adhesives, including adhesive tape, are used to attach the straight back portion, or extended fastening portion of the 6-shaped members to the patient's face in areas on both sides of the nose. This attachment secures the cannula relative to the nose. It is also convenient for allowing the patient to temporarily take off the nasal cannula simply by pulling the plugs out from the loops of the two 6-shaped members without having to tear off the adhesives.

The long leg portion of each nasal plug connects to one of the two auxiliary oxygen tubes through a tube connector. With the cannula attachment in the present invention, the patient may arrange the auxiliary oxygen tubes by, for example, looping them over the ears to reduce weight in the face area, by draping them down or using other locations. A slip loop may be optionally provided around the auxiliary oxygen tubes for cinching the tubes in front of the patient's neck. The auxiliary oxygen tubes then extend to an adapter-connector for an essentially fluid-tight connection to a main oxygen supply tube and thence to an oxygen supply device such as an oxygen tank.

In order to avoid rubbing irritation caused by the sharp edges of the plug tips, the improved cannula also preferably provides new shapes for the plug tips to achieve smoother contact with the sensitive skin inside the nostrils. Unlike the conventional plug tips where the end openings are straight tubes with sharp corners, the plug tips in the present invention advantageously have curved-in radius at the end openings where the size of the end openings are smaller than that of the body portion of the plugs. The curved-in portion of a plug tip may have, for example, a constant radius from the body portion of the plug to the end opening, a changing radius from the body portion of the plug to the end opening, and the like. A plug tip with a changing radius at the end may take a shape which resembles the nipple portion of a baby bottle.

In order to help solve the problem caused by the constant oxygen gas flow during the application of a nasal cannula, another improvement provides a pulsating gas flow, this can be accomplished by various means, including a gas flow regulator or a directional control valve. The regulator is mounted on the main oxygen supply line and controlled to provide a gas flow pattern similar to a normal respiration.

The present invention comprises an assembly for use with a nasal cannula, comprising nasal plugs for which the plug tips have a curved in radius at the end openings where the size of the end openings are smaller than the body portion of the plug. It is also a nasal oxygen or other fluid administering device wherein the location of the nasal plugs relative to eachother can be adjusted. It also includes a device for administering fluid through such an assembly at a variable flow rate pattern.

DESCRIPTION OF THE DRAWINGS

These and other features, aspects, and advantages of the present invention will become better understood with regard to the following description, appended claims, and accompanying drawings in which like members refer to like parts throughout, and where:

DETAILED DESCRIPTION OF THE PREFERRED EMBODIMENT

Figure 1:
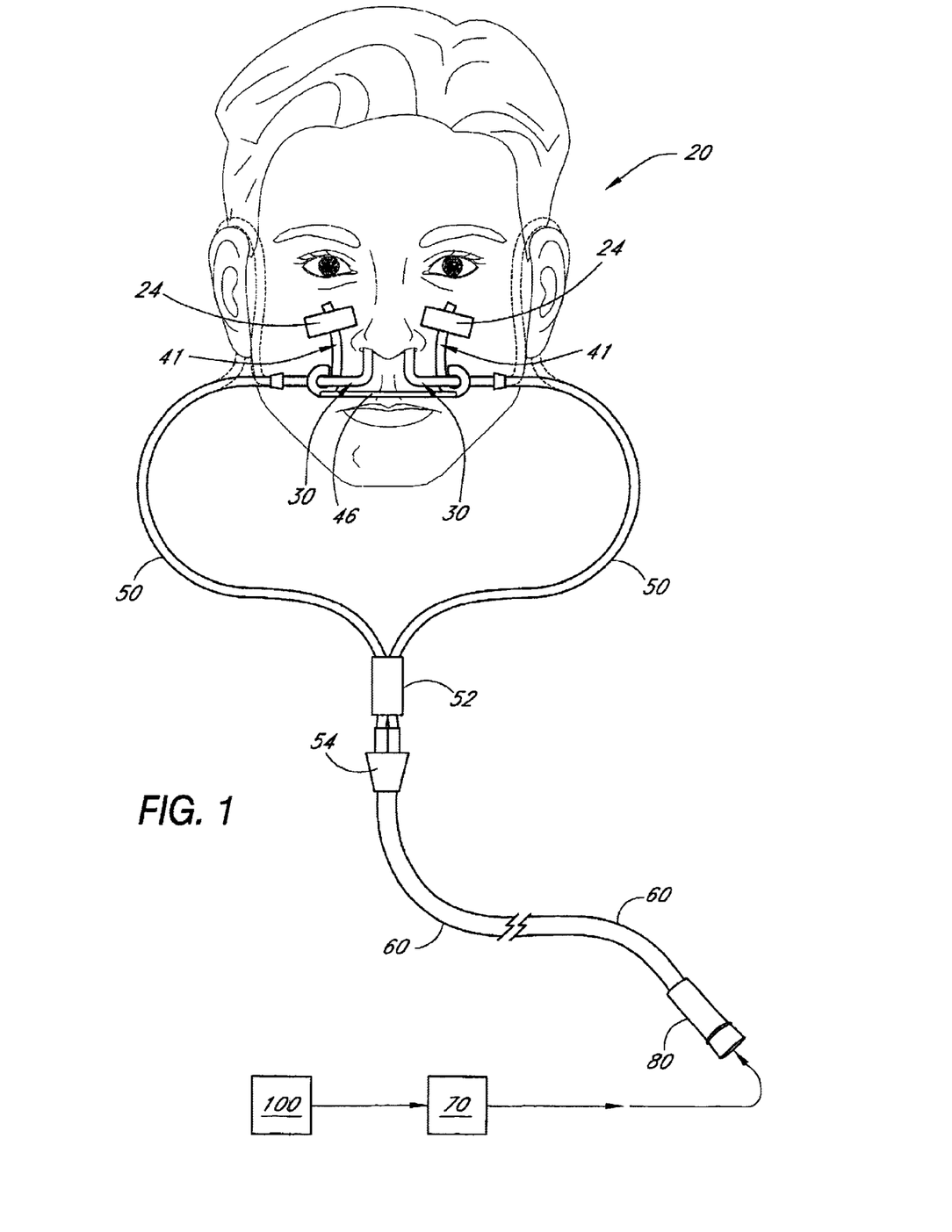
FIG. 1 shows a perspective view of a nasal cannula assembly on a patient.
Figure 2:
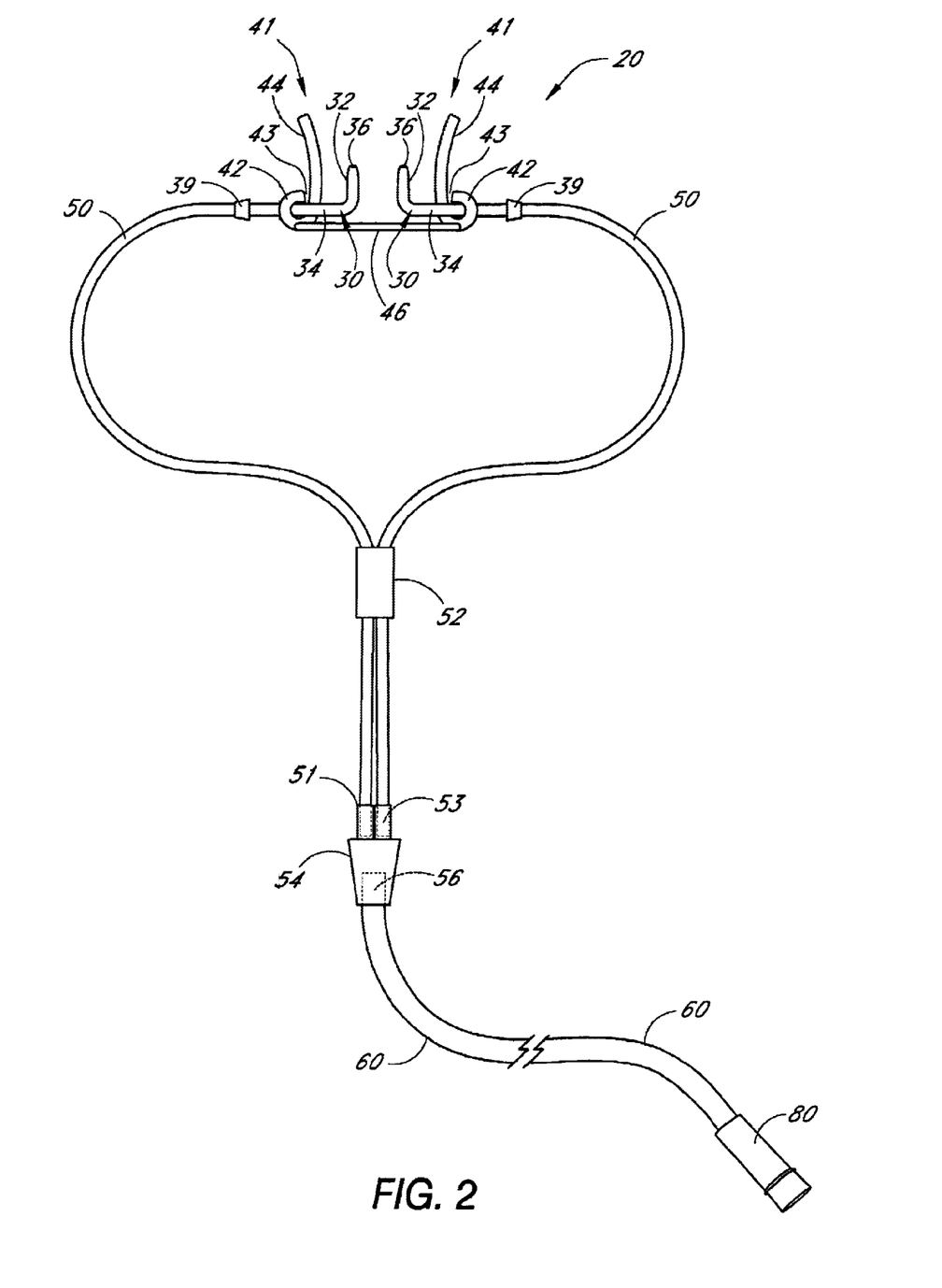
FIG. 2 shows a schematic view of a complete cannula assembly including the auxiliary and main oxygen supply tubes.

An oxygen administration system is shown in FIG. 1 and FIG. 2 as it would be worn by a patient. A nasal cannula 20 includes a pair of separated nasal plugs 30 and a connector 40. A pair of auxiliary oxygen tubes 50 are each connected to one inlet of the plugs 30. A main oxygen supply line 60 provides gas to the tubes 50 through an adapter 54 that joins auxiliary tubes 50 to supply line 60. A slip loop 52 is disposed about auxiliary tubes 50.

As shown in FIG. 1 and FIG. 2, nasal cannula 20 is configured to be positioned between the nose and the upper lip of the patient. Cannula 20 comprises a pair of separate nasal plugs 30. A nasal plug connector 40 connects the two plugs 30 and functions as a holder which can be attached to the patient's face. Each of the nasal plugs 30 is an L-shaped tube where the shorter leg portion 32 goes into patient's nostril for delivery of oxygen or other gases, and the longer leg portion 34 connects with one of the auxiliary tubes through an adapter 39. The nasal plugs 30 are preferably fabricated of injection molded polyvinylchloride having a durometer rating of about 55. The nasal plugs 30 are sized sufficiently large to provide a predetermined gas flow to the patient.

The two nasal plugs 30 are movably mounted relative to each other by having two holders 41 connected by a connecting bar 46. The bar 46 is generally straight, but may be slightly curved or bent to conform to the curvature of the patient's face. Each holder 41 advantageously comprises an attaching portion 44 and a holding portion 42. The holders 41 are preferably flexible and resemble the number "6." The holders 41 advantageously have an elongated attaching portion 44 connected to a curved holding portion 42. The holding portion 42 is preferably an annular portion, curved back toward an interior portion of the attaching portion 44. The holding portion 42 of the holders 41 may form a closed loop. Alternatively, a slot 43 can be advantageously formed in the holding portion 42, preferably at a position close to the attaching portion 44, with the slot large enough to allow the leg 34 to be removably inserted into the holding portion 42. Other configurations and types of holding portions 42 can be used as long as they allow relative motion between the holding portion 42 and nasal plug 30, to adjust the spacing between two plugs 30 to accommodate a patient's nose, yet grip the nasal plugs 30 sufficiently to hold them in position. The holding portion 42 is preferably made by a material which is flexible enough to allow the leg 34 of each L-shaped nasal plug 30 to be inserted or removed and is strong enough to hold the cannula in position during use.

The connector 40 is preferably positioned in the patient's philtrum area with the connecting bar 46 generally parallel with the patient's upper lip. The attaching portion 44 of each holder 41 is in contact with the patient's face with the loop holding portion 42 extending away from the face. The long leg 34 of each L-shaped nasal plug 30 then passes through one of the loops of holding portion 42 and points to one side of the face, with both short legs 32 pointing upward into the patient's nostrils. The holding portion 42 of each holder 41 has an elastomeric surface around at least a portion of the loop to frictionally engage one of the nasal plugs 30 This also requires the loops of holding portion 42 and legs 34 to be sized properly to achieve a good engagement. This frictional connection allows the two nasal plugs 30 to be adjusted relative to each other to change the spacing between them as well as allowing rotation along the longitudinal axis of the long legs 34 to achieve a proper orientation to advantageously center the plug tips 36 within the nostrils. Preferably the frictional engagement allows this adjustable positioning, yet maintains the final position under normal use of the nasal cannula. What constitutes a normal use of a nasal cannula can vary, but preferably the position of the nasal plugs 30 is maintained as a patient rests in bed, and further the plugs 30 will move if the supply tubes 60 or cannula 20 are moved with sufficient force that the nasal plugs 30 would hurt or injure the patient if they did not move relative to the connecting bar 46.

The connecting bar 46 bridging the two holders 41 functions as a support for the nasal cannula to maintain their relative position on the face. In particular, it helps prevent the L-shaped plugs from rotating a metial axis so the short legs 32 do not move or rock toward or away from each other to result in contact with the patient's nostrils. The frictional engagement of the plugs 30 with the holding portions 42 also restrains rotation of the plugs 30 toward and away from the patient's face, and into contact with a person's nostrils. The frictional engagement does allow adjustable positioning of the nasal plugs 30 both relative to each other along the length of connecting bar 46, and relative to a patient's face as the plugs 30 can be rotatably positioned by rotating along the longitudinal axis through bar 46 and leg portion 34.

Once the preferred depth of the plug tips 36 inside the nostrils is achieved, removable adhesives 24 are used to attach the straight attaching portion 44 of the holders 41 to the patient's face in areas on both sides of the nose. This adhesive can comprise adhesive tape, whether placed over the attaching portion 44 or elsewhere. The adhesive can also comprise a two-sided adhesive applied to the attaching portion 44. -The adhesive could also comprise a two part adhesive applied to the holders.41, such as the attaching portion 44, with an activator being applied to the holders 41, such as the attaching portion 44, or applied to the patient's face in order to activate the adhesive. Such a two part adhesive would have to be suitable for use with a person's skin.

This adhesive 24 secures the cannula relative to the nose. It is also convenient for allowing the patient to temporarily take off the nasal cannula simply by pulling the plugs 30 out from the holding portion 42 such as the loops of the two holders 41 without having to tear off the adhesives 24. Alternatively the holders 41 can be taped to the patient's face and the nasal plugs 30 adjusted to fit the nostrils as desired.

The long leg portion 34 of each nasal plug 30 connects to one of the two auxiliary oxygen tubes 50 through a tube connector 39. With the cannula attachment in the present invention, the patient may arrange the auxiliary oxygen tubes 50 by, for example, looping them over the ears to reduce weight in the face area, by draping them down over the body or chest, or other locations. A slip loop 52 may be optionally provided around the auxiliary oxygen tubes 50 for cinching the tubes in front of the patient's neck. The auxiliary oxygen tubes 50 then extend to an adapter-connector 54 for an essentially fluid-tight connection to a main oxygen supply tube 60 and thence to an oxygen supply device or other gas source 100 through a gas regulator 70.

Adapter-connector 54 is preferably provided with two outlet ports 51, 53 in a first end and a single inlet port 56 in its opposing end. The two ports 51 and 53 of adapter 54 are for receiving the ends of auxiliary tubes 50, and the single port 56 is for receiving the end of main oxygen supply line 60. The ends of auxiliary tubes extend a predetermined distance into ports 51, 53 and are advantageously connected by conventional means, including friction fitting or bonding. The end of main line 60 likewise extends a predetermined distance into port 56 and is also connected by conventional means, including friction fitting or bonding. While tubes 50 and 60 are referred to as oxygen tubes, other gases can be supplied through tubes 50 and 60, or a different gas can be supplied to each of the tubes 50.

With a nasal cannula assembled as above, oxygen or other gases can be supplied by the gas source 100, regulated to a predetermined gas flow pattern, administered through main line 60, split into auxiliary tubes 50, and fed into nostrils of the patient via the nasal plugs 30.

It is believed possible, but less desirable, to omit the holders 41 and to removably adhere the bridge or bar 46 to the patient's face, preferably in the area between the nose and lip. The previously discussed adhesives are believed suitable for this alternative application. Further, it is believed possible to apply adhesive to selected portions of the tubing 50 to removably adhere the tubing 50 to the patient's cheek or other portions of the face. This can help further stabilize movement of the nasal plugs 30.

Figure 3:
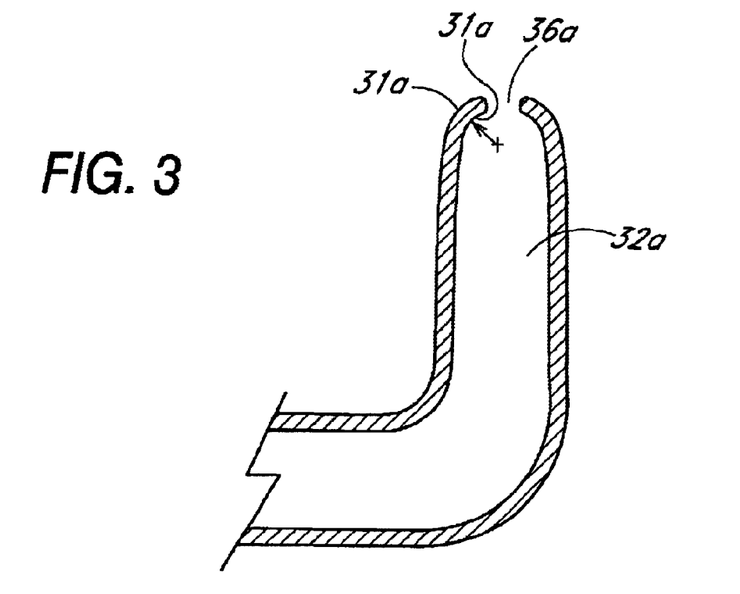
FIG. 3 and FIG. 4 show cross section views of two modified shapes of a plug tip.
Figure 4:
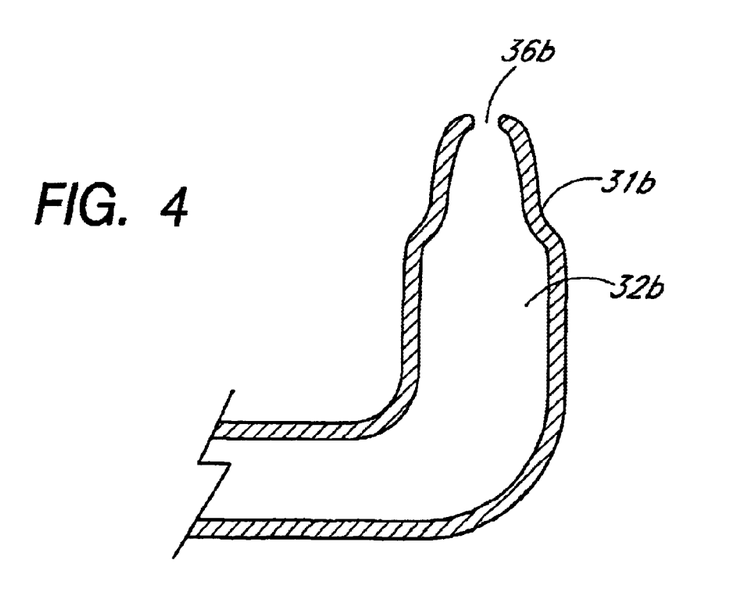

In order to further avoid rubbing irritation caused by the sharp edges of the plug tips, the improved cannula advantageously provides new shapes for the plug tips to achieve smoother contact with the sensitive skin inside the nostrils. Unlike the conventional plug tips where the end openings are straight tubes with sharp corners that can easily abrade and irritate a patient's nostrils, the plug tips in the present invention have curved-in radius at the end openings, with the size of the end openings being smaller than that of the body portion of the plugs. The curved-in portion of a plug tip may have, for example, a constant radius 31*a*, as shown in FIG. 3, from the body portion 32*a* to the end opening 36*a*; a changing radius 31*b*, as shown in FIG. 4, from the body portion 32*b* to the end opening 36*b*; and the like. A plug tip 31*b* with a changing radius at the end may take a shape which resembles the nipple portion of a baby bottle. These rounded shapes help prevent the edges of the distal ends of the nasal plugs 30 from abrading and irritating the nostrils. The curvature or shape is thus rounded enough to reduce irritation and cutting, but provides a large enough opening to provide a suitable gas flow for the patient's needs.

In a further embodiment, the oxygen or other gas that passes through the cannula 20 is controlled to vary the flow rate. Current flow rates typically provide gas at a constant flow rate, which irritates the sensitive skin in the nose, dries out localized areas, and is generally uncomfortable. By varying the flow rate the patient can be encouraged to breath with the same pattern as the gas is delivered to the cannula 20. Thus, for example, a pattern representative of relaxed breathing can be used to encourage soothing or relaxing of the patient. Patterns can be selected that are representative of a person's normal breathing pattern. Alternatively, the flow regulator or flow generator can be programmed to permit "spontaneous" breathing by the patient. During the spontaneous breathing mode, the breath rate, the tidal volume and other flow parameters are not preselected. The inspiration phase of each breath can be commenced in response to effort by the patient.

Thus, advantageously the gas flow and/or pressure is varied to simulate a desired breathing rate. Systems exist for varying the oxygen flow and pressure to masks that cover a person's nose and mouth in order to force oxygen into the lungs. An electronically controlled valve or mechanically controlled valve or flow regulator can be used to vary the flow rate of a constant gas source. One example would be using a stepper motor to control a valve on a constant pressure gas source. The stepper motor can be controlled electronically or mechanically to vary the flow rate. Alternatively, an electronically controlled or mechanically controlled device can generate a variable gas flow. Further, both the flow rate and pressure can be varied by means known in the art.

In general, flow to the patient during inspiration is governed by a flow control valve. When the flow control valve opens, pressurized gas is introduced to the cannula 20, through the nostrils and into the patient's lungs. Preferably, a flow regulator or flow generator capable of operating in several modes is desired so that the degree of support that the cannula 20 provides to the patient's natural breath patterns can be varied. The predetermined flow parameters include the tidal volume, or the volume of gas which is inhaled by the patient during each breath; the breath rate, which is the number of breaths per minute; the peak flow rate, which is the maximum flow rate of the gas delivered to the patient during inspiration; and the breath profile, which is the shape of the curve in a flow rate versus time graph. The most significant of these parameters is often the tidal volume, since, depending on size and age of the patient, the tidal volume can vary significantly.

A variety of devices can be used to provide the variable flow and pressure to the cannula 20. For example, U.S. Pat. No. 5,315,989, the contents of which are incorporated by reference, discloses a medical ventilator having a flow-control valve that controls the inspiratory flow and pressure. Feedback signals provided to the valve's controller provide inspiratory closed-loop flow control and pressure control.

Similarly, U.S. Pat. No. 4,440,116, the contents of which are incorporated by reference, discloses a variable-orifice valve for adjustment of the peak flow rate. It also has a waveform regulator that supplies controlled gas pressure to the orifice. It is believed possible to modify this device to provide a variable flow rate, and/or a variable pressure, to the nasal cannula 20.

Further devices and methods are illustrated by U.S. Pat. No. 5,494,028, the contents of which are incorporated herein by reference. In that patent, a medical ventilator has a valve which controls the flow of gas from a pressurized gas source to a patient for inhalation. The same principles can be adapted for varying the gas flow through cannula 22. Flow through the valve is choked and pressure upstream of the valve is held stable so that a known relationship exists between the position of the valve and the flow rate through the valve. An open loop control system causes the valve to open or close as needed to deliver a preselected tidal volume of gas to the patient on each breath. Since the flow rate is known, no feedback to the controller regarding actual flow conditions is required. The exact positioning of the valve and length of time that the valve is to be held open is predetermined by the controller before the breath is delivered, and is repeated for subsequent breaths. Preferably, the valve is driven by a stepping motor, and the controller comprises a microcomputer. The controller compensates for ramping of the stepping motor as the valve opens and closes in determining the positions of the valve required to deliver the preselected tidal volume.

Additionally, ventilators, such as the one described in U.S. Pat. No. 4,527,557, the contents of which are incorporated by reference, have used a microcomputer controller which receives input regarding the desired flow parameters and compares these preselected parameters with actual flow conditions to control the opening and closing of a flow control valve to vary the flow rate of the gas to the patient.

Referring to FIG. 1, one mechanical way of obtaining a repeatable pattern of variable gas flow is to pinch the main gas supply tube 60 with a gas flow regulator or a multi-lobed cam 70. The cam 70 pinches the supply tube 60 to reduce and vary the flow as the cam 70 is rotated by a motor. The number, size and location of the lobes on the cam 70 can be varied to achieve a variety of flow alterations, and the rotation of the cam can also be varied. As illustrated, other electronic and mechanical devices can be used to vary the flow rate and pressure.

Figure 5:
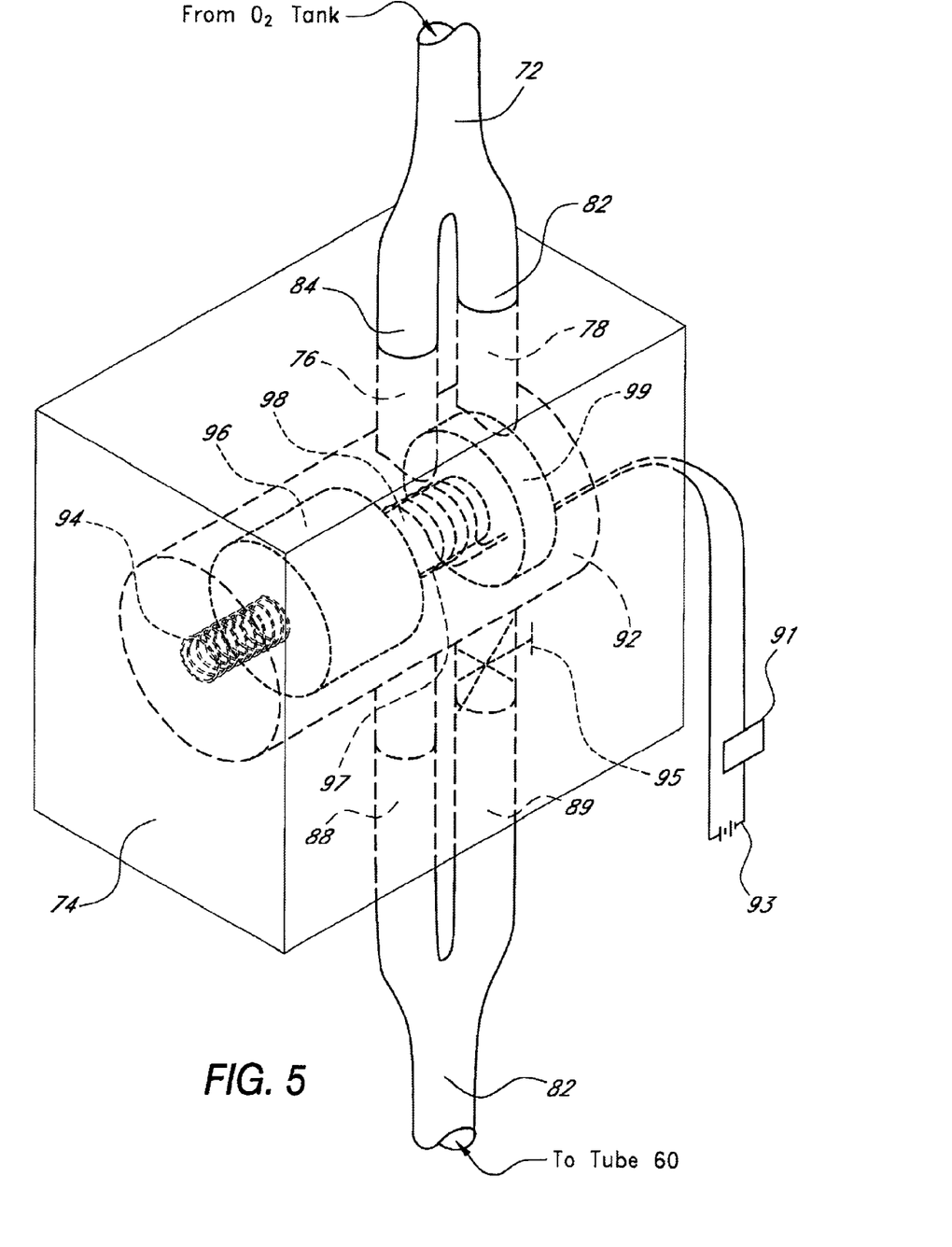
FIG. 5 shows a perspective view of a gas flow regulator for providing the pulsating oxygen flow.

Referring to FIG. 5, another way of obtaining a controlled gas flow is to use a directional control valve. The valve is made by encasing a plate 74 with two ports, Port A 84 and Port B 86 where each port has an inlet 76, 78, and an outlet 88, 89. The inlet 76 and outlet 88 are preferrably coaxial, and parallel to coaxial inlet 78 and outlet 89. Outside of the plate, there are two "Y" shaped connectors 72 and 82, one connecting the oxygen tank with both inlet A 76 and inlet B 78, the other one connecting outlet A 88 and outlet B 89 to the main oxygen supply line 60 which connects with the nasal cannula 20.

Inside the plate 74, the inlet and outlet of both ports are connected by a channel 92 that extends between, and preferably orthogonal to the coaxial paths 76, 88 and 78, 89. A spring 94 is mounted with one end connected to an end of the channel 92 and a reciprocating valve is attached to the other end of the spring. The valve consists of three portions with different cross section dimensions. Two opposing end portions 96 and 99 have the same dimension and an intermediate portion 98 has a smaller dimension than that of portions 96 and 99. The preferred shape of the valve is cylindrical, with the ends 96, 99 having a larger diameter than middle portion 98.

A solenoid coil 97 is connected to the valve to reciprocate the valve in channel 92. The solenoid is wound on the small diameter portion 98 of the valve with the two ends in electrical connection with a control circuit 91 powered by battery 93, where the control circuit 91 has a timer which provides a signal to turn the power to the coil "ON" and "OFF" with a predetermined frequency to regulate the pulsation to the respiratory rate. This frequency can be adjusted according to the reparation pattern of the patient's need.

When the spring 94 is at the relaxed position, the larger spool portion 96 blocks flow from inlet 76 and its outlet 88 and the smaller portion 98 is at the flow path between inlet 78 and outlet 89 to allow flow there between. When the solenoid is energized, the middle portion 98 is at the low path between inlet 76 and outlet 88 to allow oxygen flow from inlet 76 through outlet 88.

The outlet 89 is fitted with a safety control valve 95. The valve 95 can be made either a manual control valve or a electrical control valve. In the event of battery failure or failure of electrical components, the spring 94 returns the solenoid to the relaxed position and end 96 blocks flow from inlet 76 to outlet 88. The valve 95 on outlet 89 is opened either manually or electrically and continuous flow of oxygen is available. When the safety control valve 95 is made an electrically controlled valve, the valve can be released open when a signal is sent by the control circuit 91 when needed. This may also be desirable in the event of heavy exertion or the need for extra oxygen. When the system is shut off, this oxygen flow would be available by leaving the valve 95 on outlet 89 open. The solenoid and battery can be encased in a plastic case to make it explosion proof. Thus, during normal use the solenoid 97 moves valve end 96 to control flow from inlet 76 to outlet 88 and hence to the patient, at a predetermined rate. If the power fails, the solenoid 97 is deactuated and spring 94 opens alternative flow path 78, 89 which can provide gas to the patient when valve 95 is opened.

The above disclosure and examples are given by way of example, not limitation. Thus, given the above disclosure, other insubstantial variations will be apparent to those skilled in this area, which variations use the spirit of the invention disclosed herein. Further, the above description uses the various features in combination, but it is to be understood that each of the described features can be used separately from the others, or can be used in combination with one or more of the features described herein.

What is claimed is:

1. An assembly for use with a nasal cannula, comprising:
   a first and second nasal plug each having a gas inlet and a nostril outlet prong configured for insertion into a patient's nostril and through which gas can pass, the inlets of the two nasal plugs being adapted to be placed in fluid communication with a gas supply;
   a first holder connected to the first nasal plug and a second holder connected to the second nasal plug; and
   a connector connected to each of the holders, the first and second plugs being independently and movably mounted to the first and second holders, respectively, the plugs being selectively movable relative to each other and the connector along and about an axis generally transverse to an axis of the patient's nostril;
   wherein at least one of the first and second holders comprises a holding portion frictionally engaging at least one of the nasal plugs sufficiently to maintain a selected linear position and angular orientation of the plug along and about the transverse axis under normal use of the nasal cannula yet allow linear and rotational movement of the plug along and about the transverse axis upon application of a friction-overcoming force to adjust a relative spacing between the plugs and the angular orientation of the plugs while the plus,s remain in contact with the respective holders.

2. An assembly as defined in claim 1, wherein the first and second holders further comprise an attaching portion connected to the holding portion, and the attaching portion is adapted to be removably fastened to a patient's face.

3. An assembly as defined in claim 2, wherein the connector is adapted to be removably fastened to a patient's face with adhesive.

4. An assembly as defined in claim 3, wherein a gas supply is placed in fluid communication with the inlet of at least one of the nasal plugs.

5. A nasal cannula as defined in claim 3, wherein a shape of each plug consists of a straight tube with a changing curvature connecting to the end opening that resembles a nipple portion of a baby bottle.

6. An assembly as defined in claim 1, wherein the connector further comprises a bar and the holders are movably fastened to either a gas supply connected to the inlet of a nasal plug, or are movably fastened to the nasal plug.

7. An assembly as defined in claim 1, wherein edges of the nostril outlet pronges each have inwardly curved surfaces leading to edges forming openings through which gas passes in exciting the outlet prongs.

8. A nasal cannula as defined in claim 1, further comprising a gas source in fluid communication with the nasal plugs, and a device for varying at least one of a pressure or a flow rate of the gas to the nasal plug according to a predetermined pattern.

9. A nasal cannula as defined in claim 8, wherein the device for varying the flow rate of the gas further comprising a two-port directional control valve with a first and a second inlet, a first and a second outlet where the first inlet and the first outlet are aligned in a first line and the second inlet and the second outlet are aligned in second line in parallel with the first line with a spacing between the first line and the second line, and two Y-shaped connectors, one of the Y-shaped connectors adapted to connect to the gas source with said first and second inlet of said directional control valve, the other said Y-shaped connector adapted to connect said first and second outlet of said directional control valve to a main oxygen supply line which connects to the nasal cannula.

10. A nasal cannula as defined in claim 9, wherein the directional control valve further comprising a central elongated channel with a sufficient length which is perpendicular to and in communication with said inlets and outlets, a spring with one end attached to one end of said channel on one side, a valve connected to the other end of said spring, and a solenoid to reciprocate the valve in the channel to vary the gas flow, the solenoid being in electrical connection with a control circuit, where the control circuit has a timer which provides a signal to turn the power to the solenoid on and off with a preset frequency.

11. A nasal cannula as defined in claim 10, wherein the valve has a three-portion shape with a first portion, a second portion and a third portion connected to each other, and with the first portion connected to the spring, where the first and the third portions have a larger dimension than that of the second portion, the larger dimension being smaller than that of the channel so that the valve can reciprocate inside of and along the channel.

12. A nasal cannula as defined in claim 10, wherein the first portion of the valve is at the first line blocking the flow from first inlet to the first outlet and the second portion of the valve is at the second line position while the spring is at a relaxed position when the solenoid is at an "OFF" status, and wherein the second portion of the valve is at the first line position with the spring being compressed when the solenoid is at an "ON" status which allows the gas flowing from the first inlet through the first outlet.

13. A nasal cannula as defined in claim 9, wherein the directional control valve further comprises a safety control valve located in the second outlet.

14. A nasal cannula as defined in claim 13, wherein the safety control valve is a manual valve.

15. A nasal cannula as defined in claim 13, wherein the safety control valve is an electrically controlled valve connected to the control circuit, and the safety control valve can be opened when a signal is sent by the control circuit.

16. A nasal cannula assembly, comprising:
  a first and second nasal plug each having an apertured nostril outlet prong each configured to be inserted into a patient's nostril, and a gas inlet extending at an angle to the outlet prong and adapted to be placed in fluid communication with a gas supply; and
  a connector extending between the plugs a length sufficient to allow the plugs to be placed in a patient's nostrils, the plugs being movably mounted relative to each other and the connector along and about an axis generally transverse to an axis of the patient's nostril so that a spacing between the plugs along the transverse axis is selectively adjustable and the rotational position of each plug about the transverse axis is selectively adjustable, the plugs being held to the connector sufficiently to maintain a selected position and orientation of the plugs during normal use of the cannula.

17. An assembly as defined in claim 16, wherein the nasal plugs are mounted to the connector by a holder connected to the connector and forming a frictional contact with the nasal plugs sufficient to hold a position and orientation of the nasal plugs relative to the connector.

18. An assembly as defined in claim 17, further comprising an elongated and flexible attaching portion connected to the holder and adapted to be removably and adhesively secured to a patient's face during use of the cannula.

19. An assembly as defined in claim 18, wherein the first and second holder each comprise an annular portion having a slot of sufficient size that the slot provides access for inserting and removing the nasal plugs into the annular portion.

20. An assembly as defined in claim 18, wherein the first and second holder each comprise an annular portion having an elastomeric surface around at least a segment of the annular portion and located to frictionally engage one of the nasal plugs passing therethrough.

21. An assembly as defined in claim 17, further comprising a gas source in fluid communication with the nasal plugs, and a device for varying at least one of a pressure or a flow rate of the gas to the nasal plug according to a predetermined pattern.

22. An assembly as defined in claim 16, wherein the plug outlet openings have edges that are rounded sufficiently to reduce irritation of a patient's nostril.

23. A method of providing gas to a patient through a nasal cannula, comprising the steps of:
  placing at least one of a first and second nasal plug in fluid communication with a gas source, and inserting each nasal plug into a patient's nostril;
  movably connecting each nasal plug to a respective holder, the holders being connected by a connector that maintains a desired space between the holders, each of the holders being configured to frictionally engage a respective plug sufficiently to maintain a spacing and orientation of each plus relative to the patient's nostrils and the other plug during normal use, the plugs being selectively movable relative to each other and the connector along and about an axis generally transverse to an axis of the patient's nostril;

removably fastening one of the holder or connector to a patient's face; and selectively applying force to at least one plug to move the plug relative to the holder while the holder or connector remains fastened to the patient's face and the at least one plug remains inserted in the patient's nostril.

24. A method as defined in claim 23, wherein the holder has an elongated portion and the fastening step comprises adhering the elongated portion to the face of the patient.

25. A method as defined in claim 24, wherein the elongated portion of the holder is adhered to the patient's face with an adhesive.

26. A method as defined in claim 24, wherein each holder comprises a slot configured to accept a portion of the corresponding plug, the slot comprising an elastomeric surface adapted to frictionally engage the portion of the plug.

27. A method as defined in claim 23, comprising the further step of placing a gas in fluid communication with the nasal cannula, and varying at least one of a flow rate or a pressure of the gas provided to the nasal plugs.

28. The method of claim 23 additionally comprising applying force to at least one plug to rotate the plug within the holder so as to change the angular position of the plug relative to the transverse axis.

29. An assembly for use with a nasal cannula, comprising:

a first and second nasal plug each having a gas inlet and a nostril outlet configured for insertion into a nostril and through which gas can pass, the inlets of the two nasal plugs being adapted to be placed in fluid communication with a gas supply; and a connector comprising a first holder and a second holder, at least one of the first and second holders comprising a holding portion frictionally engaging at least one of the nasal plugs sufficiently to maintain a selected linear position and angular orientation of the plug along and about an axis generally transverse to an axis of the nostril under normal use of the nasal cannula yet allow linear and rotational movement of the plug along and about the transverse axis upon application of a friction-overcoming force to adjust a relative spacing between the plugs and the angular orientation of the plugs without removing the nostril outlet from the patient's nostril.

30. An assembly as defined in claim 29, wherein the first and second holders are connected to each other by a bridge member, and each of the holders comprises an elongate attachment portion adapted to be releasably secured to a patient's face.

31. An assembly as defined in claim 30, wherein the elongate attachment portion is configured to be secured to a patient's face with an adheive.

32. An assembly as defined in claim 30, wherein the nasal plugs can be removed from the holding portions without the holding portions being removed from the patient's face.

33. An assembly for use with a nasal cannula, comprising:

a first and second nasal plug each having a gas inlet and a nostril outlet prong configured for insertion into a nostril and through which gas can pass, the inlets of the two nasal plugs being adapted to be placed in fluid communication with a gas supply;

a first holder connected to the first nasal plug and a second holder connected to the second nasal plug;

a connector connected to each of the holders, the plugs being movably mounted relative to each other and the connector;

a gas source in fluid communication with the nasal plugs; and a device for varying at least one of a pressure or a flow rate of the gas to the nasal plug according to a predetermined pattern;

wherein at least one of the first and second holders comprises a holding portion frictionally engaging at least one of the nasal plugs sufficiently to maintain a selected linear position and angular orientation of the plug along and about an axis of the connector under normal use of the nasal cannula yet allow linear and rotational movement of the plug along and about the axis of the connector to adjust a relative spacing between the plugs and the angular orientation of the plugs; and wherein the device comprises a two-port directional control valve with a first and a second inlet, a first and a second outlet where the first inlet and the first outlet are aligned in a first line and the second inlet and the second outlet are aligned in second line in parallel with the first line with a spacing between the first line and the second line, and two Y-shaped connectors, one of the Y-shaped connectors adapted to connect to the gas source with said first and second inlet of said directional control valve, the other said Y-shaped connector adapted to connect said first and second outlet of said directional control valve to a main oxygen supply line which connects to the nasal cannula, the directional control valve further comprising a central elongated channel with a sufficient length which is perpendicular to and in communication with said inlets and outlets, a spring with one end attached to one end of said channel on one side, a valve connected to the other end of said spring, and a solenoid to reciprocate the valve in the channel to vary the gas flow, the solenoid being in electrical connection with a control circuit, where the control circuit has a timer which provides a signal to turn the power to the solenoid on and off with a preset frequency.

34. A nasal cannula as defined in claim 33, wherein the valve has a three-portion shape with a first portion, a second portion and a third portion connected to each other, and with the first portion connected to the spring, where the first and the third portions have a larger dimension than that of the second portion, the larger dimension being smaller than that of the channel so that the valve can reciprocate inside of and along the channel.

35. A nasal cannula as defined in claim 33, wherein the first portion of the valve is at the first line blocking the flow from first inlet to the first outlet and the second portion of the valve is at the second line position while the spring is at a relaxed position when the solenoid is at an "OFF" status, and wherein the second portion of the valve is at the first line position with the spring being compressed when the solenoid is at an "ON" status which allows the gas flowing from the first inlet through the first outlet.

* * * * *

UNITED STATES PATENT AND TRADEMARK OFFICE
CERTIFICATE OF CORRECTION

PATENT NO. : 6,763,832 B1
DATED : July 20, 2004
INVENTOR(S) : Wolff M. Kirsch et al.

It is certified that error appears in the above-identified patent and that said Letters Patent is hereby corrected as shown below:

<u>Title page,</u>
Item [75], Inventors, delete "Andes, NY" and insert -- Hemet, CA --.

<u>Column 9,</u>
Line 4, delete "plus,s" and insert -- prongs --.
Line 25, delete "pronges" and insert -- prongs --.

<u>Column 11,</u>
Line 4, delete "plus" and insert -- plug --.
Line 18, delete "the" and insert -- an --.
Line 61, delete "adheive" and insert -- adhesive --.

Signed and Sealed this

Second Day of May, 2006

JON W. DUDAS
*Director of the United States Patent and Trademark Office*